United States Patent
Arêdes Martins et al.

(10) Patent No.: US 12,270,021 B2
(45) Date of Patent: Apr. 8, 2025

(54) DEVICE AND METHOD FOR MICROORGANISM CELL DISRUPTION BY EXTRUSION

(71) Applicants: PETRÓLEO BRASILEIRO S.A.—PETROBRAS, Rio de Janeiro (BR); UNIVERSIDADE FEDERAL DE VIÇOSA, Viçosa (BR)

(72) Inventors: Marcio Arêdes Martins, Viçosa (BR); Dilson Novais Rocha, Viçosa (BR); Mauricio De Oliveira Leite, Viçosa (BR); Bruno Bezerra Vieira, Viçosa (BR); Rafael Richard João, Rio de Janeiro (BR); Leonardo Brantes Bacellar Mendes, Rio de Janeiro (BR)

(73) Assignees: Petróleo Brasileiro S.A.—PETROBRAS, Rio de Janeiro (BR); Universidade Federal De Viçosa, Florianópolis (BR)

( * ) Notice: Subject to any disclaimer, the term of this patent is extended or adjusted under 35 U.S.C. 154(b) by 1206 days.

(21) Appl. No.: 16/980,322

(22) PCT Filed: Mar. 8, 2019

(86) PCT No.: PCT/BR2019/050074
§ 371 (c)(1),
(2) Date: Sep. 11, 2020

(87) PCT Pub. No.: WO2019/173888
PCT Pub. Date: Sep. 19, 2019

(65) Prior Publication Data
US 2021/0115388 A1    Apr. 22, 2021

(30) Foreign Application Priority Data
Mar. 13, 2018 (BR) ................ 10 2018 004973 9

(51) Int. Cl.
*C12M 1/00* (2006.01)
*C12M 1/02* (2006.01)
(Continued)

(52) U.S. Cl.
CPC ........... *C12M 47/06* (2013.01); *C12M 33/00* (2013.01); *C12M 41/18* (2013.01); *C12M 41/40* (2013.01); *C12M 41/48* (2013.01); *C12N 1/066* (2013.01)

(58) Field of Classification Search
CPC ...... C12M 47/06; C12M 33/00; C12M 41/18; C12M 41/40; C12M 41/48; C12M 1/33;
(Continued)

(56) References Cited

U.S. PATENT DOCUMENTS 3,298,061 A * 1/1967 Pomper .................. B29C 48/34
                                                          417/497
4,249,703 A   2/1981 Korenev et al.
(Continued)

FOREIGN PATENT DOCUMENTS

BR    PI0500597 A     5/2006
BR    112013032547 A2 1/2017
(Continued)

OTHER PUBLICATIONS

Uematsu, T., et al., WO 2016/092828 A1, published Jun. 16, 2016, original and machine translation (Year: 2016).*
(Continued)

*Primary Examiner* — Michael L Hobbs
(74) *Attorney, Agent, or Firm* — ARENTFOX SCHIFF LLP

(57) ABSTRACT

Aspects are provided in relation to devices and systems for microorganism cell wall disruption. In this scenario, a device is provided for cell disruption of a microorganism suspension comprising (i) an inlet duct (1) of microorgan-
(Continued)

isms, (ii) an annular channel (13) downstream of inlet duct (1) and in communication therewith, adapted for disruption of microorganism cells, the annular channel (13) being formed by an external part (7) and an internal part (8), the internal part being positioned inside the cavity formed by the external part (7) and (iii) an outlet duct (9) downstream of annular channel (13) and in communication therewith, for output of the ruptured microorganisms. A method is further provided that is associated with the device described above.

13 Claims, 2 Drawing Sheets

(51) Int. Cl.
    *C12M 1/26*     (2006.01)
    *C12M 1/34*     (2006.01)
    *C12M 1/36*     (2006.01)
    *C12N 1/06*     (2006.01)

(58) Field of Classification Search
    CPC ...... C12M 45/02; C12M 45/20; C12M 23/50; C12M 33/12; C12N 1/066; C11B 1/04
    See application file for complete search history.

(56) References Cited

U.S. PATENT DOCUMENTS

2006/0011755 A1*   1/2006   Ando .................... B01F 35/714
                                                   241/1
2017/0327766 A1    11/2017   Uematsu et al.

FOREIGN PATENT DOCUMENTS

| EP | 0303791 A1 * | 2/1989 | ............... C12N 1/06 |
| JP | 2013172677 A | 9/2013 | |
| WO | WO-2012175999 A1 * | 12/2012 | ............ C12M 47/06 |
| WO | WO-2016092828 A1 * | 6/2016 | ............. B02C 19/06 |

OTHER PUBLICATIONS

International Search Report & Written Opinion for PCT/GB2019/050074 mailed May 10, 2019.

Wang et al (2018), Microalgal cell disruption via extrusion for the production of intracellular valuables. Energy, v. 142, p. 339-342, Jan. 2018.

Edebo, L. Disintegration of cells by extrusion under pressure. In. Enzyme Technology, Springer-Verlag, p. 93-114-, 1982.

* cited by examiner

DEVICE AND METHOD FOR MICROORGANISM CELL DISRUPTION BY EXTRUSION

CROSS-REFERENCE TO RELATED APPLICATIONS

This application is a United States National Stage Application of co-pending International Patent Application Number PCT/BR2019/050074 filed 8 Mar. 2019, which claims priority to BR 10 2018 004973 9, filed 13 Mar. 2018, the contents of which are incorporated herein by reference in their entireties.

FIELD OF THE INVENTION

The present invention is related to devices and systems for the disruption of the cell wall of microorganisms. In particular, the present invention is related to devices and systems for the disruption of the cell wall of microalgae.

BACKGROUND

Microalgae are recognized as an excellent source of proteins, lipids, polyunsaturated fatty acids, carotenoids, pigments and vitamins and can be used in the food, feed, cosmetics, pharmaceutical and biofuel industries. As a source of energy, they are a promising alternative for the production of biofuels, when compared with other conventional energy crops. Their photosynthetic efficiency, associated with rapid growth and the production of lipids, makes their use possible in the production of biofuels, such as ethanol, hydrogen and biodiesel.

Microalgae, like cyanobacteria, are competitive organisms for use in industrial applications, since they exhibit rapid cell growth and have basic nutritional needs (sunlight, water and $CO_2$) and elevated mutation rates, thus ultimately presenting great potential for genetic modification. Because of their natural diversity and ability to grow in a variety of habitats, there is a growing need to exploit these microorganisms in the production of biofuels and food, especially in areas of low agricultural value.

Rupture of the cell wall of the microalgae is necessary to extract the intracellular metabolites of interest. Several methods of cell disruption for extraction of these compounds of interest are disclosed in scientific articles, such as the use of ultrasound, microwaves, mechanical processes (use of high-pressure homogenizers and mills), chemical processes (solvents and acids), high temperatures (autoclave), freezing and thawing cycles, and extraction by supercritical fluids and ionic liquids.

Mechanical disruption using homogenizers with pressures from 305.9 to 1529.5 $kgf/cm^2$ (300 to 1500 bar) has been successful in large-scale applications due to greater extraction yield when compared to other methods. However, high energy consumption is a limitation in terms of use of this technology to extract products with low added value.

The document "Show, K. Y., Lee, D. J., Tay, J. H., Lee, T. M., Chang, J. S., Microalgal drying and cell disruption" presents a comparison of cell disruption methods utilizing:
(i) a high-pressure press, which is efficient in cell disruption but requires considerable energy, making its use impracticable on a large scale due to the high operating costs;
(ii) a ball mill, which consists of a practical method for large-scale mechanical cell disruption, but the degree of cell disruption depends upon the characteristics of the grinding elements, and its large-scale application requires a large amount of energy;
(iii) the ultrasound technique, which favors extraction in a short time and reduces the use of solvents, but the high energy consumption and the difficulty of large-scale use are negative factors;
(iv) extraction with supercritical fluids, which does not produce toxic waste and employs solvents from renewable sources, but the high energy consumption, high cost of implementation and difficulties in scaling up make the technology impracticable in the biofuel scenario; and
(v) enzymatic extraction, which is used in combination with other cell disruption methods for greater extraction efficiency and for more resistant organisms, but has high operating costs due to the cost of the enzymes.

Also cited is the cryogenic process, which is easy to use and does not require a solvent, but large-scale use results in high operating costs, making the process impracticable.

The microalgae oil extraction system documented in U.S. Pat. No. 8,043,496 B1 proposes rupturing the microalgal cell wall after pumping and impact against deflectors. Following this stage, the liquid phase flows into a tank where three phases will presumably be formed: oils, wastewater and biomass. However, damage to the cell structure depends on the diameter and species of the microalgae. However, there is no information in this document on the working pressure level.

The high-pressure homogenizers used in the dairy industry can be adapted for cell disruption of microalgae and have as advantages the possibility of working with algal biomass with high solids content and continuously. The mechanisms of cell disruption by the homogenizer are not completely understood but have been attributed to pressure variation, shear stress, inertial forces, shock, turbulence and cavitation.

High pressures from 305.9 to 1529.5 $kgf/cm^2$ (300 to 1500 bar) are required in the homogenizers with a hydraulic dwell time of 30 minutes to 3 hours. Because of high energy consumption, large scale use of cell disruption with a homogenizer is of questionable economic viability for production of biofuels. Moreover, the temperature increase occurring in homogenizers can interfere with the physicochemical quality of the compounds of interest, such as proteins and unsaturated oils. In addition, adjustment is made according to the required pressure level and not according to the size of the cells of the microalgae species being processed.

As will be detailed below, the present invention seeks to solve the problems of the prior art described above in a practical and efficient manner.

SUMMARY OF THE INVENTION

The primary object of a preferred embodiment of the present invention is to provide a device and method for mechanical disruption of cells of microorganisms by extrusion, using low pressures from 76.5 to 153.0 $kgf/cm^2$ (75 to 150 bar), and therefore reduced energy consumption.

The preferred embodiment of the present invention has the secondary object of producing a device and method for cell disruption allowing regulation of the system, depending on the species and size of the microorganisms.

The preferred embodiment of the present invention has the tertiary object of providing a device and method for cell disruption of microorganisms, comprising a cooling system to avoid loss of physicochemical properties of the material extracted by cell disruption.

To realize the aforementioned objects, the preferred embodiment of the present invention provides a device for disruption of microorganism cells by extrusion, comprising (i) an inlet duct of a suspension of microorganisms, (ii) an annular channel downstream of the inlet duct and in communication therewith, adapted for disruption of microorganism cells, the annular channel being formed by an external part and an internal part, the internal part being positioned inside the cavity formed by the external part and (iii) an outlet duct downstream of the annular channel and in communication therewith for output of the ruptured cells.

The preferred embodiment of the present invention also provides a method for disruption of microorganism cells by extrusion, comprising the steps of (i) promoting the forced flow of a suspension of microorganisms through an annular channel downstream of an inlet duct and in communication therewith, the annular channel being adapted for disruption of the microorganism cells and being formed by an external part and an internal part, the internal part being positioned inside the cavity formed by the external part; and (ii) driving the ruptured cells through an outlet duct downstream of the annular channel and in communication therewith.

BRIEF DESCRIPTION OF THE FIGURES

The detailed description presented below refers to the attached figure and its respective reference numbers.

DETAILED DESCRIPTION OF THE INVENTION

Preliminarily, it is emphasized that the description that follows starts from a preferred embodiment of the invention. However, the invention is not limited to this particular embodiment.

Figure 1:
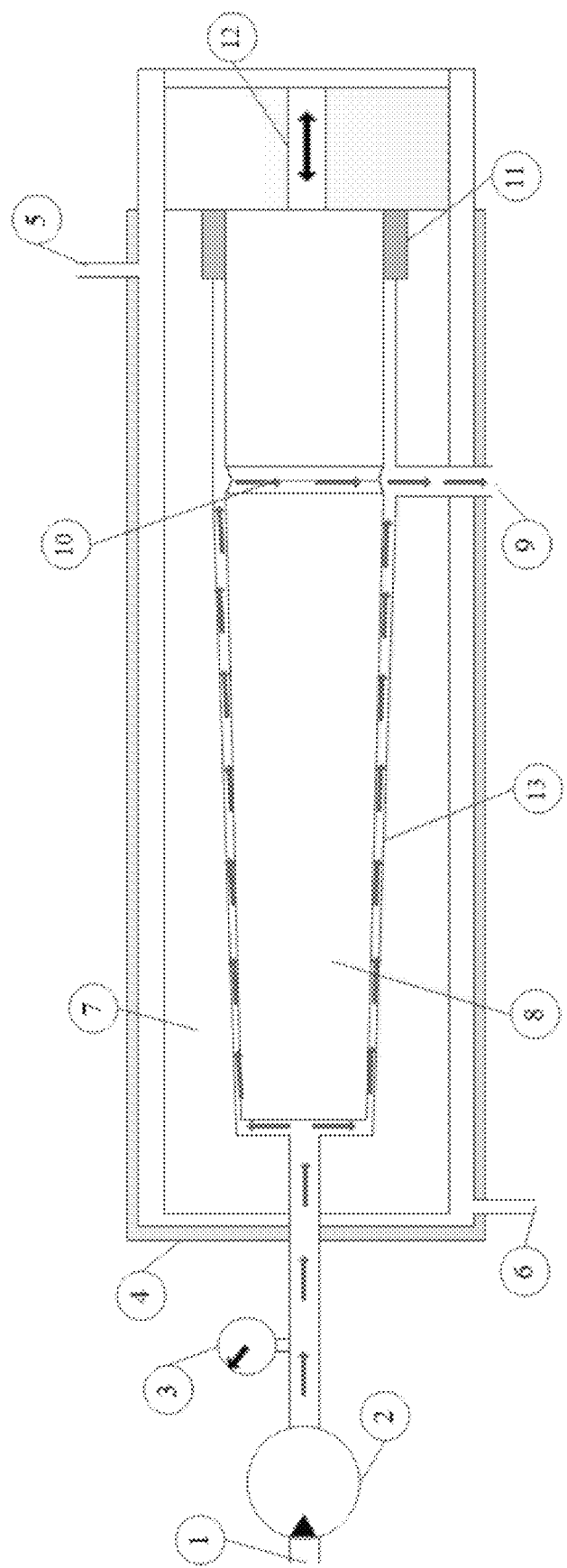
FIG. 1 shows a cross section of the device according to a preferred embodiment of the present invention.

FIG. 1 shows a cross section of the device according to a preferred embodiment of the present invention. The cell disruption device of the preferred embodiment of the present invention comprises an inlet duct 1 of a suspension of microorganisms. An annular channel 13 is provided downstream of the inlet duct 1 and in communication therewith, whose size can be adjusted according to the species and diameter of the microorganism, for disruption or cells by extrusion, as will be seen below.

The stream of the microorganisms is forced into the annular channel 13 so that the cell walls are ruptured by extrusion. The forced flow into the annular channel 13 is preferably promoted by means of a positive displacement pump 2, preferably positioned in inlet duct 1.

A pressure gauge 3 is preferably provided at any point between point 2 and annular channel 13 to measure the inlet pressure of the device.

Alternatively, a negative displacement pump (not shown) is used in the device downstream of the annular channel 13 to draw the suspension of microorganisms into the device.

The annular channel 13 is formed by an external part 7 and an internal part 8, the internal part 8 being positioned inside the cavity formed by the external part 7. Internal part 8 preferably has precisely the same cavity-shaped shape formed by external part 7 so that the annular channel 13 has essentially parallel walls. More preferably, external part 7 has a female truncated cone shape. The internal part 8 in this embodiment has the same truncated cone shape but with a male fitting.

The internal part 8 is optionally adjustable with respect to the inner cavity formed by the external part 7 by means of an adjustment mechanism 12 to regulate the diameter of annular channel 13. Moreover, the adjustment mechanism 12 can be a pneumatic, hydraulic, mechanical, electric or manual adjustment mechanism. Activation of the adjustment mechanism 12 can also be formed by a combination of at least two types of drive.

An automated control system is optionally provided to control adjustment mechanism 12.

The device of the preferred embodiment of the present invention further comprises an outlet duct 9 downstream of annular channel 13 and in communication therewith for the output of ruptured cells.

Internal part 8 preferably comprises a cavity 10 positioned near outlet duct 9. This cavity 10 has the function of generating a low-pressure zone at this point and directing the flow of ruptured material to outlet duct 9. More preferably, cavity 10 is aligned with the outlet duct, as shown in FIG. 1.

The device of the preferred embodiment of the present invention preferably also includes a sealing element 11 positioned at the end of the annular channel 13 opposite inlet duct 1 in the vicinity of adjustment mechanism 12. Sealing element 11 is preferably a gasket made of flexible material.

To avoid an excessive increase in temperature of the microorganism suspension, a cooling system is preferably provided in the device of the preferred embodiment of the present invention. The system comprises a cooling jacket 4 positioned around the external part 7.

The cooling system also includes a coolant input 5 to inject coolant into cooling jacket 4 and a coolant output 6 to remove coolant from cooling jacket 4. The coolant inlet 5 is preferably positioned longitudinally and transversely away from the coolant output 6 to promote coolant flow throughout virtually the entire cooling jacket 4 and external part 7.

The external part 7 is preferably made from a heat-conductive material, such as metal, permitting efficient heat exchange between the coolant and the microorganism suspension.

The preferred embodiment of the present invention also provides a method for disruption of microorganism cells, comprising the steps of:

(i) promoting a forced flow of a suspension of microorganisms through an annular channel 13 downstream of an inlet duct 1 and in communication therewith, the diameter of the annular channel 13 being adapted for cell disruption and formed by an external part 7 and internal part 8, the internal part 8 being positioned inside the cavity formed by external part 7; and (ii) passing the ruptured microorganisms through an outlet duct 9 located downstream of annular channel 13 and in communication therewith.

The method of the preferred embodiment of the present invention also preferably includes the step of adjusting the position of the internal part 8 in relation to the cavity formed by the external part 7 by an adjustment mechanism 12 in order to regulate the diameter of annular channel 13.

The method of the preferred embodiment of the present invention preferably comprises the additional step of cooling the microorganism suspension inside annular channel 13 by means of a cooling system. More preferably, the step of cooling the microorganism suspension includes the circulation of a coolant through cooling jacket 4.

The preferred embodiment of the present invention therefore provides a device and method for cell disruption of a microorganism suspension by extrusion, using low pressures from 76.5 to 153.0 kgf/cm$^2$ (75 to 150 bar) and thus reduced energy consumption. The device of the preferred embodiment of the present invention even permits the regulation of the diameter of the annular channel as a function of the diameter and width of the cells of the microorganisms, making it fully and efficiently adapted to disruption of the species of interest.

The cooling system also prevents the loss of physicochemical properties of the extracted material.

To demonstrate the efficiency of the proposed device and method, the disruption of cells of the species *Scenedesmus obliquus* BR003 was carried out with the preferred embodiment of the present invention. Flow cytometry (BD Facsverse, BD Biosciences) analysis was used to check cell disruption. The analysis revealed that a cycle of five passes at a pressure of 127.5 kgf/cm$^2$ (125 bar) was sufficient to cause damage to the cell structure, reducing the relative size of the cells (FSC—forward scatter, FIG. 2) by about 50% when compared to the control (without disruption).

Figure 2:
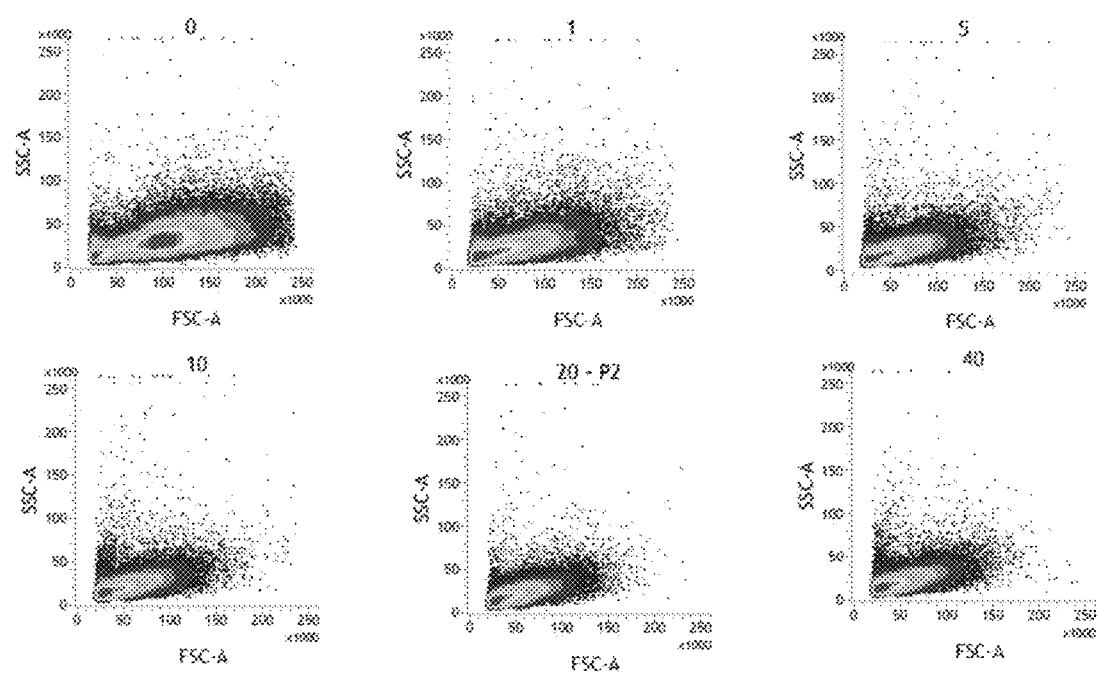
FIG. 2 shows results of application of the device and method of the preferred embodiment of the present invention, more specifically a result of analysis of flow cytometry in the microalgae *Scenedesmus obliquus* BR003 without rupture (0) and with a number of passes of 1, 5, 10, 20 and 40.

In addition to the relative size of the cells, there was also a reduction in granulosity, observed by the parameter SSC (SSC—side scatter, FIG. 2). This parameter depends on the internal complexity of the particle, for example, shape of the nucleus, number and type of cytoplasmic granules and roughness of the membrane. Thus, the reduction of this parameter indicates that there was a reduction in the number of intact cells, producing cell fragments (debris). The statistical analyses shown in Table 1 indicated that the variation in number of passes through the device, between 10 and 40, did not result in a significant difference in relative cell size.

TABLE 1

| Number of passes | SSC-A average | FSC-A average | FSC-A SD | FSC-A VC (%) | FSC-A median |
|---|---|---|---|---|---|
| 0 | 34,806 | 111,871 | 50,149 | 44.8 | 109,368 |
| 1 | 27,016 | 73,560 | 39,442 | 53.6 | 66,187 |
| 5 | 23,658 | 62,318 | 31,500 | 50.6 | 55,724 |
| 10 | 22,739 | 59,217 | 29,629 | 50.0 | 52,950 |
| 20 | 21,507 | 57,099 | 27,496 | 48.2 | 51,431 |
| 40 | 21,840 | 57,063 | 27,858 | 48.8 | 51,025 |

It should be noted that the FSC index shown in Table 1 is related to cell size. SSC is related to internal complexity of the cells and SD and VC correspond to standard deviation and variation coefficient (%), respectively.

Numerous variations on the scope of protection of this application are possible. This reinforces the fact that the present invention is not limited to the particular configurations/embodiments described above.

The invention claimed is:

1. A device for cell disruption of microorganisms by extrusion, characterized in that the device comprises:
    an inlet duct for a microorganism suspension;
    an annular channel downstream of the inlet duct and in communication therewith, adapted for disruption of microorganism cells, the annular channel being formed by an external part and an internal part, the internal part being positioned inside a cavity formed by the external part;
    a pump adapted to pump a suspension of microorganisms through the annular channel; and
    an outlet duct downstream of the annular channel and in communication therewith, for output of ruptured cells, wherein
    the internal part is adjustable with respect to the inner cavity formed by the external part by an adjustment mechanism to regulate the diameter of the annular channel.

2. The device according to claim 1, characterized in that the pump is a positive displacement pump positioned in the inlet duct.

3. The device according to claim 1, characterized in that the position of the internal part is adjustable with respect to the cavity formed by the external part by means of an adjustment mechanism in order to regulate the diameter of the annular channel.

4. The device according to claim 3, characterized in that the adjustment mechanism is at least one pneumatic, hydraulic, mechanical, electric, or manual device.

5. The device according to claim 1, characterized in that the device further includes one pressure gauge adapted to check the inlet pressure of the device.

6. The device according to claim 3, characterized in that the device further includes an automated control system adapted to control the adjustment mechanism.

7. The device according to claim 1, characterized in that the internal part comprises part of the channel positioned near the outlet duct.

8. The device according to claim 7, characterized in that the device further comprises a sealing element adapted to seal the end of the annular channel opposite the inlet duct.

9. The device according to claim 1, characterized in that the device additionally includes a coolant system, comprising:
    a cooling jacket positioned around the external part;
    a coolant input adapted to inject coolant into the cooling jacket; and
    a coolant outlet adapted to remove coolant from the cooling jacket.

10. Method for cell disruption of microorganisms by extrusion, characterized in that the method includes the steps of:
    promoting a forced flow of a suspension of microorganisms through a device comprising an inlet duct and an annular channel downstream of the inlet duct and in communication therewith, the annular channel being adapted for disruption of microorganism cells and formed by an external part and an internal part, the internal part being positioned inside a cavity formed by the external part, a pump adapted to prompt the forced flow of the microorganisms through the annular channel; and
    an outlet duct downstream of the annular channel and in communication therewith, for output of ruptured cells, wherein
    the internal part is adjustable with respect to the inner cavity formed by the external part by an adjustment mechanism to regulate the diameter of the annular channel; and
    passing the ruptured cells through the outlet duct.

11. Method according to claim 10, characterized in that the method includes the additional step of adjusting the position of the internal part in relation to the cavity of the external part by means of an adjustment mechanism in order to regulate the diameter of the annular channel as a function of the species and diameter of the microorganisms.

12. Method according to claim 10, characterized in that the method includes the additional step of cooling the suspension of microorganisms inside the annular channel by means of a cooling system.

13. Method according to claim 12, characterized in that the cooling step of the microorganism suspension includes circulation of coolant through a cooling jacket.

* * * * *